United States Patent
Ritz

(10) Patent No.: US 11,363,803 B2
(45) Date of Patent: Jun. 21, 2022

(54) ARTIFICIAL HABITAT FOR BENEFICIAL INSECTS

(71) Applicant: Nicole Keller Ritz, Seattle, WA (US)

(72) Inventor: Nicole Keller Ritz, Seattle, WA (US)

( * ) Notice: Subject to any disclaimer, the term of this patent is extended or adjusted under 35 U.S.C. 154(b) by 120 days.

(21) Appl. No.: 16/672,446

(22) Filed: Nov. 2, 2019

(65) Prior Publication Data

US 2021/0127644 A1 May 6, 2021

(51) Int. Cl.
| | | |
|---|---|---|
| *A01K 67/033* | (2006.01) | |
| *A01K 47/04* | (2006.01) | |
| *A01K 47/06* | (2006.01) | |
| *A01K 49/00* | (2006.01) | |

(52) U.S. Cl.
CPC ............ *A01K 67/033* (2013.01); *A01K 47/04* (2013.01); *A01K 47/06* (2013.01); *A01K 49/00* (2013.01)

(58) Field of Classification Search
CPC ...... A01K 49/00; A01K 67/033; A01K 47/00; A01K 47/04; A01K 47/06
See application file for complete search history.

(56) References Cited

U.S. PATENT DOCUMENTS

| | | | | |
|---|---|---|---|---|
| 3,191,199 A | * | 6/1965 | Barnes, Jr. ............. | A01K 47/00 449/4 |
| 4,557,005 A | * | 12/1985 | Rossmo ............... | A01K 67/033 449/56 |
| 5,618,220 A | * | 4/1997 | Mills ...................... | A01K 47/00 449/4 |
| 2019/0075762 A1 | * | 3/2019 | Kapka .................... | A01K 47/02 |

OTHER PUBLICATIONS

Large Bee Block Nester Hotel Solitary Bee Hive House n Charcoal; Brand: Green & Blue; Amazon.co.uk website: https://www.amazon.co.uk/Large-Block-Nester-Solitary-Charcoal/dp/B07Q61FTQ9, accessed Aug. 20, 2021; published Apr. 2, 2019. (Year: 2019).*

* cited by examiner

*Primary Examiner* — Daniel J Colilla

(57) ABSTRACT

This invention discloses an artificial habitat site for beneficial insects. The habitat is made by stacking grooved bricks on top of one another to create cavities or tunnels for insects to nest, shelter, or overwinter. The bricks are made from durable and reusable materials that are easy to maintain and sanitize.

1 Claim, 4 Drawing Sheets

ARTIFICIAL HABITAT FOR BENEFICIAL INSECTS

BACKGROUND

Beneficial insects provide valuable services to plants and include pollinators, predators, and parasitic predators. Pollinating insects are a crucial group in nearly all terrestrial ecosystems, and helping them is essential to our continued survival, health, and well-being. Loss of natural habitat due to increased urbanization, intensive agriculture, pollution, wide-spread use of pesticides, climate change, fungus, parasites, and disease have all had a negative impact on native pollinator and other beneficial insect populations. Providing additional habitat sites for nesting, shelter, and overwintering for these beneficial insects helps increase their populations and in turn helps with pollination and pest control.

Artificial nesting sites have been created solely for targeting solitary wood nesting bees, which only comprise approximately 30% of our 4,000 North American Native bee species.

Artificial nesting sites for wood nesting bees have been created by drilling holes in blocks of wood, but the inner nest surface cannot be exposed for cleaning or sterilization. Additionally, they tend to become contaminated over time with diseases, parasites, mold and fungus and must be regularly replaced.

Devices made from grooved boards which are secured together to form bee nesting sites have also been used. These systems of wooden trays are highly susceptible to warping, and pest attacks. Once moisture has warped any of the trays even slightly, it allows for the spread of disease, parasites, mold, and fungus.

Devices made from synthetic materials such as Styrofoam and plastic have problems attracting bees, could potentially leach harmful chemicals, have poor durability, and retain moisture inside resulting in mold, mildew, and fungus problems.

Both wooden and synthetic blocks require aggressive sanitation between seasons to prevent spread of disease, pest infestations, mold, and fungus. This usually requires harsh chemicals that could leave harmful residue.

Single use disposable nesting tubes have been created out of paper and cardboard, but these tubes need to be protected from the elements and moisture. Therefore, an additional device or structure is needed to protect the nesting tubes from the environment.

All of the aforementioned nesting systems are susceptible to predator attacks. Rodents and birds can easily destroy the wood, paper, cardboard, plastic and Styrofoam blocks to prey on the insects.

BRIEF SUMMARY OF THE INVENTION

These and other embodiments of the disclosed invention provide an artificial habitat site that is environmentally friendly, reusable, durable, resistant to moisture, rot, elemental damage, warping, pest infestation, and bird and rodent attacks. They provide easy access to the tunnels for inspection of the insects. They are easy and inexpensive to sanitize and maintain. Some embodiments of the bricks can be boiled in water or heated to clean and sanitize without the need for any potentially harmful chemicals.

Additional benefits were discovered during the creation of these embodiments. They are also resistant to UV damage and deterioration, thermal/moisture expansion and thermal shock, and fire damage. They can be naturally tinted to aid in attracting beneficial insects, and patterns can be imprinted on the side to aid insect navigation.

The durable nature of these embodiments allows them to be placed directly in contact with the soil and open to the elements without requiring additional protective coverings.

These systems are easy to maintain and are not only useful to solitary wood nesting bees, but a multitude of beneficial insects and encourage biodiversity.

The following groups of beneficial insects have been known to use pre-existing tunnel like cavities for nesting, shelter, and/or overwintering. These beneficial insects include, but are not limited to:
Wood- and Tunnel-Nesting Solitary Bees (*hymenoptera*)
Ground-Nesting Solitary Bees (*hymenoptera*)
Potter Wasps (*hymenoptera*)
Pollen Wasps (*hymenoptera*)
Digger and Sand Wasps (*hymenoptera*)
Syrphis Flies/Hoverfly (*diptera*)
Butterflies (*lepidoptera*)
Moths (*lepidoptera*)
Lacewings (*neuroptera*)
Ladybirds/Ladybugs (*coleoptera*)

DRAWING—REFERENCE NUMERALS

Figure 1:
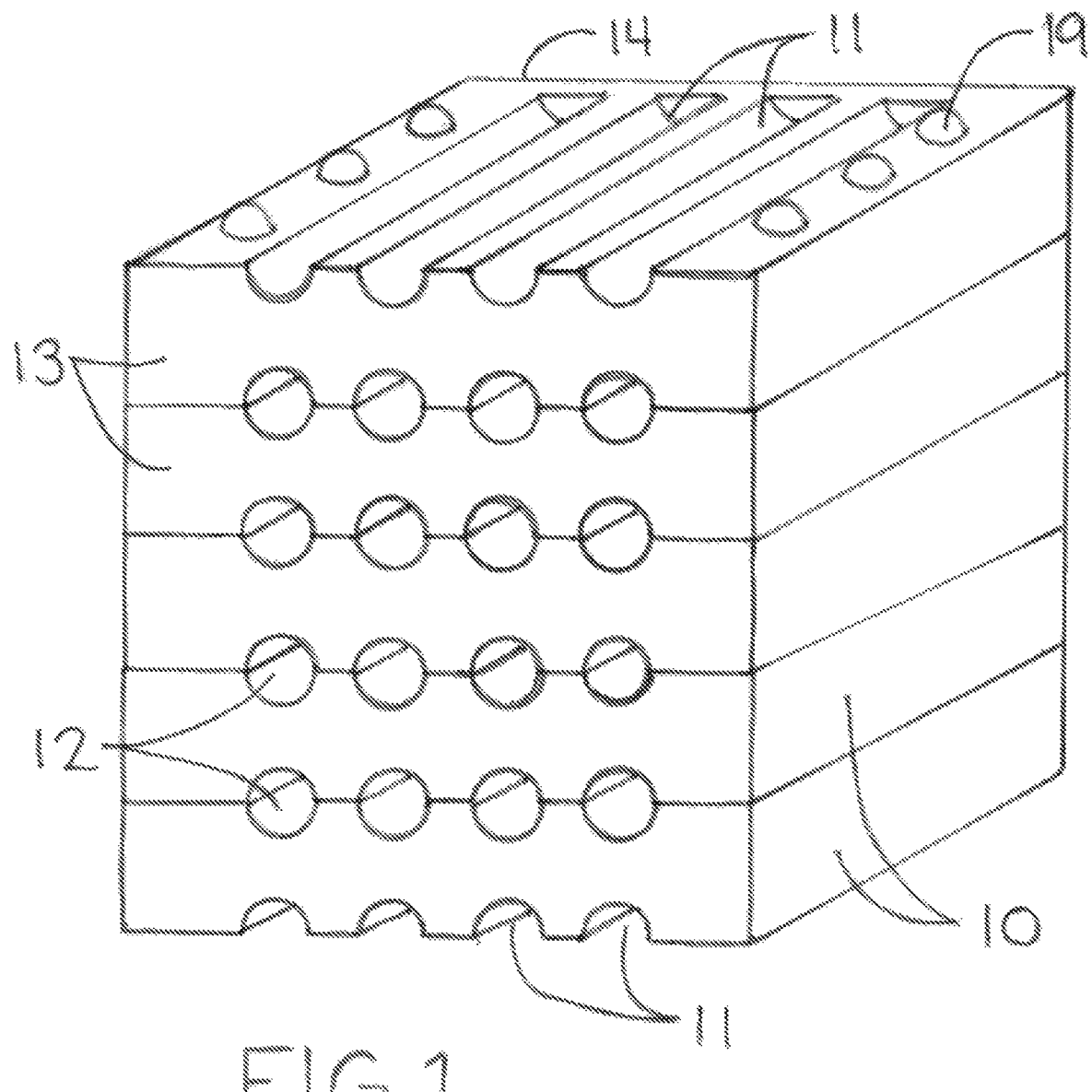
FIG. 1 is a detailed front perspective view showing an embodiment of a plurality of prismatic bricks in assembled position with furrows aligned to form artificial habitat sites.
Figure 3:
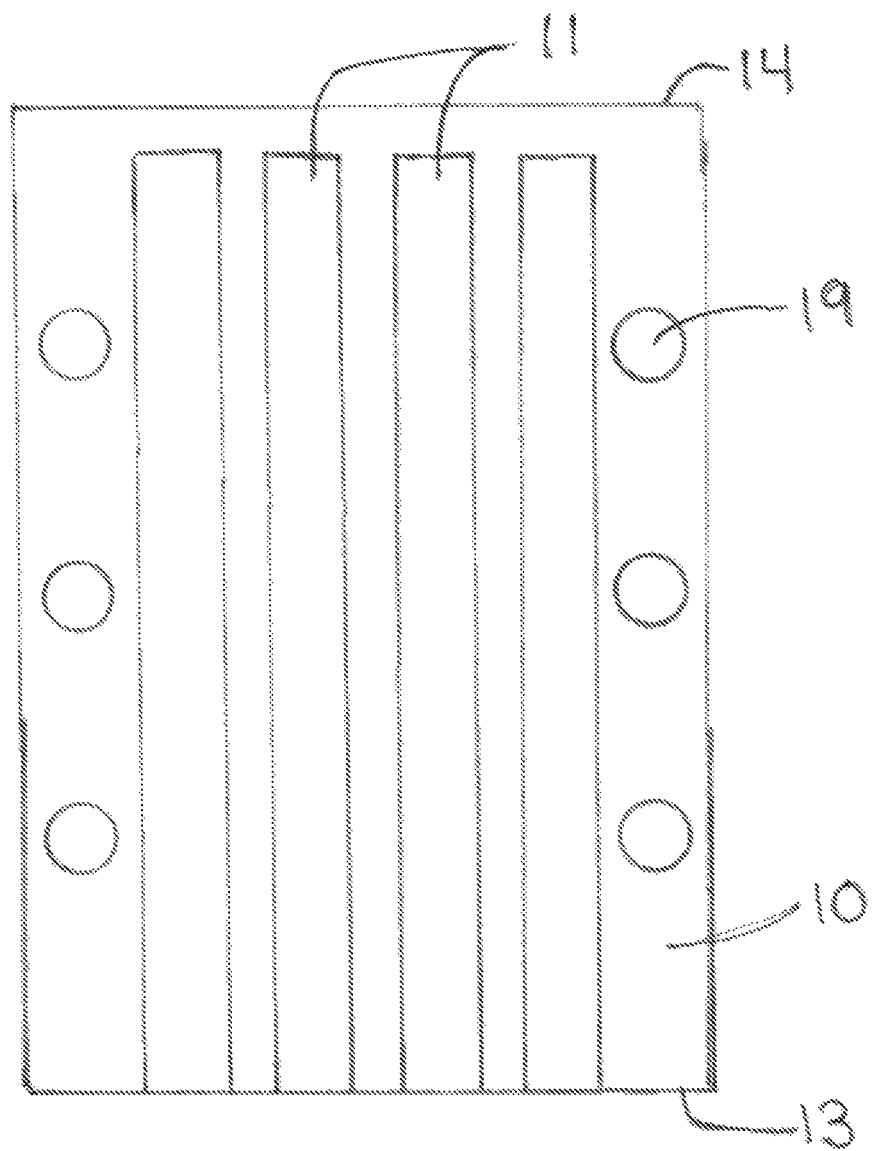
FIG. 3 is showing the top of one of the prismatic brick embodiments used in constructing the artificial habitat.
Figure 2:
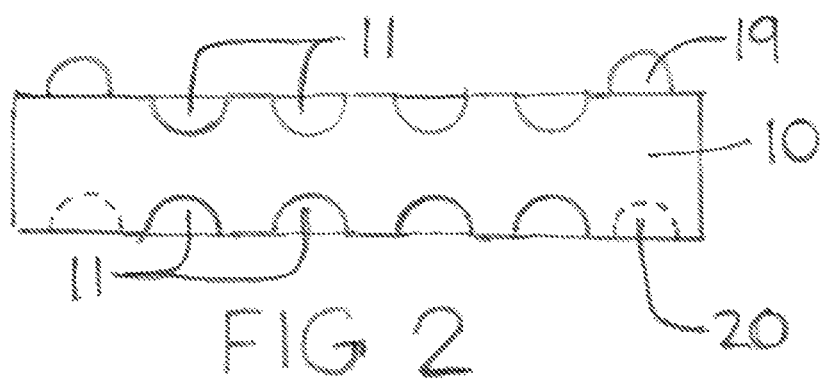
FIG. 2 is a front view showing one of the prismatic brick embodiments used in constructing the artificial habitat.
Figure 4:
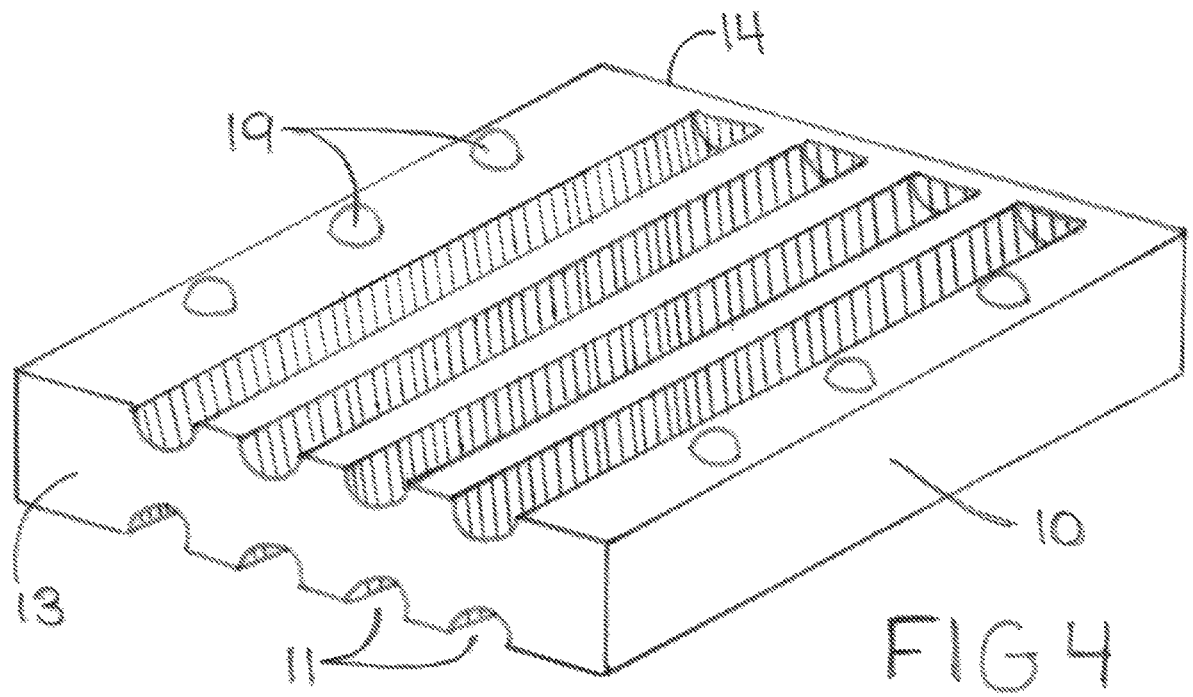
FIG. 4 is a detailed front perspective view showing one of the prismatic brick embodiments used in constructing the artificial habitat.
Figure 5:
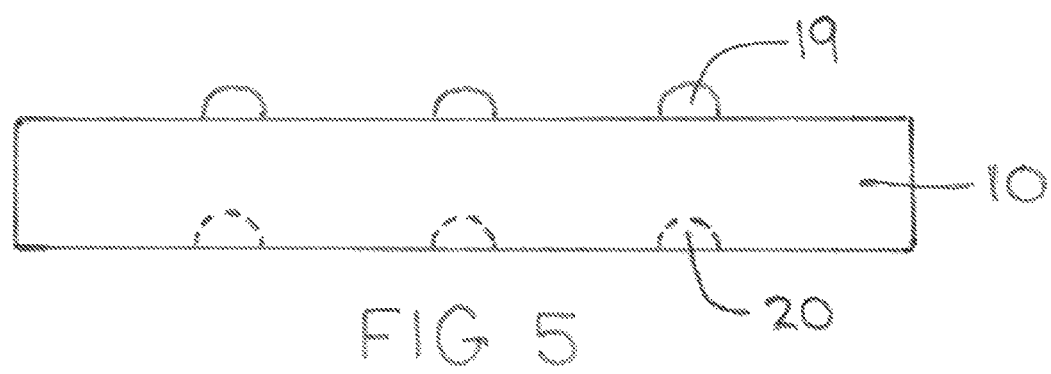
FIG. 5 is showing the side of one of the prismatic brick embodiments used in constructing the artificial habitat.

10 brick
11 furrows, grooves
12 cavity, tunnel, hole, habitat site
13 front face
14 back face
15 top face
16 bottom face
17 countersunk furrow entrance at front face
18 angled furrows
19 projections
20 recessions

DETAILED DESCRIPTION OF THE INVENTION

Referring now to FIGS. 1-7, the present invention provides an artificial habitat for beneficial insects. The artificial habitat in FIG. 1 is generally made up of a plurality of bricks stacked on top of one another, as shown in FIG. 1.

When the bricks (10) are stacked together, as shown in FIG. 1, the furrows (11) on adjacent bricks align to form a cavity or tunnel (12) to be used as an artificial habitat site.

Figure 6:
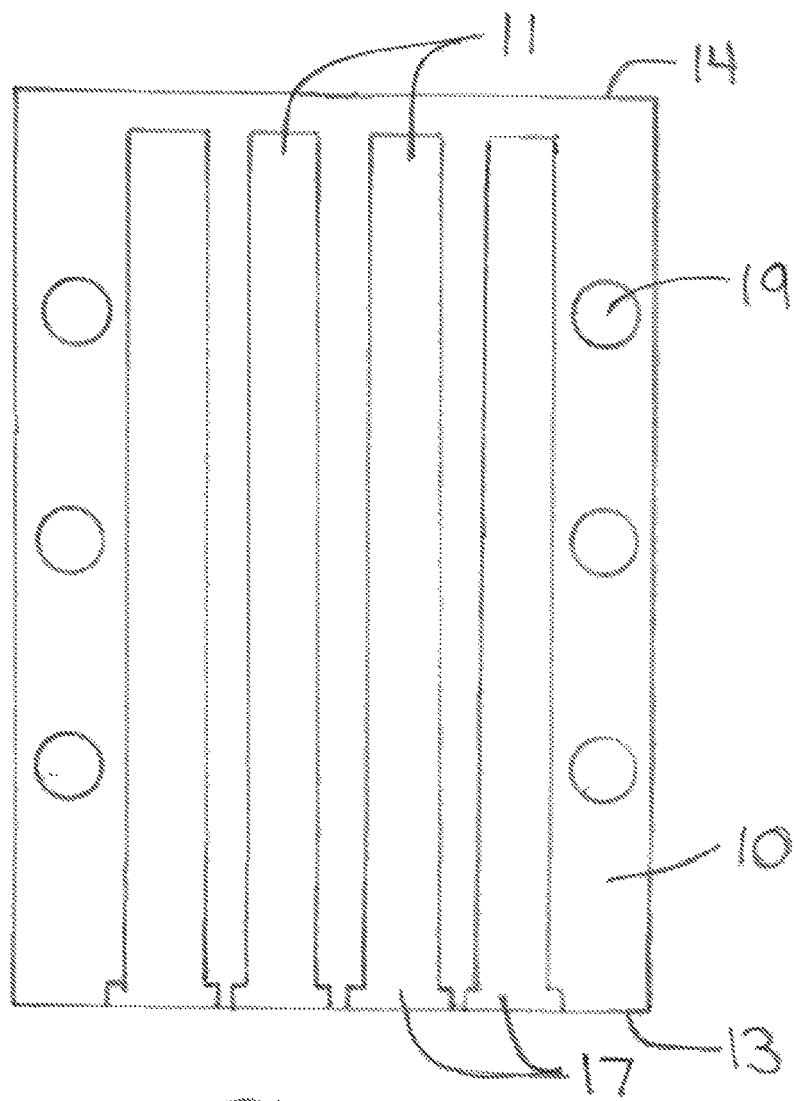
FIG. 6 is showing the top of an alternate embodiment of the prismatic brick with countersunk furrow opening.
Figure 7:
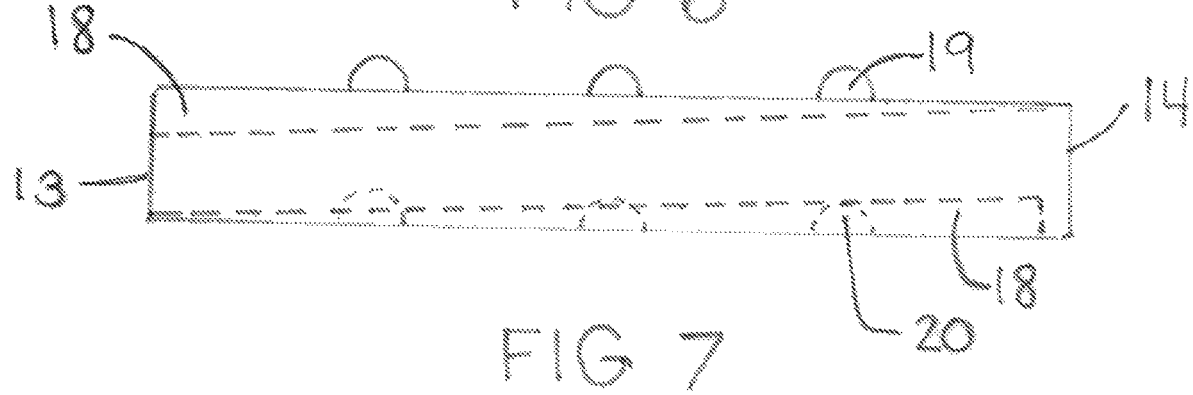
FIG. 7 is a cross-sectional view of an alternate embodiment of the prismatic brick with downward angled furrows.

Furrows (11) have an open end on the front face (13) extending toward the back face (14). While the furrows (11) can extend from the front face (13) to the back face (14), the preferred furrow embodiment terminates short of the back face (14) for better protection from the environment, pests, and predators, as shown in FIG. 1 through FIG. 7. While there can be any number of furrows (11) in a variety of arrangements, FIG. 1 through FIG. 4, and FIG. 6 depict 4 furrows (11) on the top face of the bricks (15) and 4 furrows (11) on the bottom face of the brick (16). Different widths of furrows (11) can be used in the same bricks (10) as to form habitats desirable to a variety of beneficial insects. While the furrows (11) can be any desirable widths, the preferred widths range from 3/32" to 3/8" in diameter, to attract beneficial insects. While the furrow cross-sections (11) can be curved or polygonal, FIG. 1 through FIG. 4, and FIG. 6 show a curved embodiment. The furrow end at the front face can be countersunk (17), as shown in FIG. 6 widening the entrance to facilitate a landing space for insects. The furrows can be angled down toward the front face of the bricks (18) to facilitate drainage, as shown in FIG. 7.

The bricks can take a variety of shapes, such as cylindrical or prismatic, as shown in FIG. 1 through FIG. 7. While the dimensions of the bricks can vary, the preferred embodiment should be such that the length of the furrows (11) are 3" to 6" in length. The bricks (10) can have a plurality of projections (19) on the top face (15), and a plurality of corresponding recessions (20) on the bottom face (16). Such that when the bricks are stacked, as shown in FIG. 1, the projections (19) fit into the recessions (20) and prohibit lateral movement. There can be any number of corresponding projections (19) and recessions (20), FIG. 2 through FIG. 7 depict 6 projections (19) on the top face of the bricks (15) and 6 recessions (20) on the bottom face of the bricks (16).

While the projections (19) and recessions (20) can be any corresponding, interlocking shapes, FIG. 2 through FIG. 7 depict a hemisphere shape.

In accordance with the preferred embodiment, the bricks that stack together to form the artificial habitat are produced by extruding, molding, casting, pressing, or milling a clay body into the specially shaped bricks. Then kiln firing said bricks into ceramic.

The bricks are then stacked on top of one another, as shown in FIG. 1, and placed outside in the desired beneficial insect habitat site. In each of these embodiments described above, accessibility is provided for inspection, cleaning, and maintenance.

I claim:

1. A method of forming an artificial habitat for beneficial insects, said habitat consisting of stacked specially shaped ceramic bricks, said method comprising the steps of:
   providing a clay body;
   extruding, molding, casting, pressing, or milling said clay body into specially shaped bricks; and
   kiln firing said specially shaped bricks into ceramic bricks,
   wherein each brick includes a first side and a second side, opposite the first side, where the first side and second side each have a plurality of half-cylindrical recesses, the first side has a plurality of projections, and the second side has a plurality of recesses such that when two bricks are arranged together each half-cylindrical recess on the first side and a respective one of the half-cylinder recess on the second side form a full, cylindrical tunnel to provide a habitat for insects, and the plurality of projections on the first side each fit into a respective one of the plurality of recesses on the second side thereby preventing lateral movement of the bricks with respect to one another.

* * * * *